United States Patent

Compton et al.

Patent Number: 6,160,151
Date of Patent: Dec. 12, 2000

[54] PROCESS FOR PRODUCTION OF DIPHENYL-DIALKOXYSILANE, PHENYLALKYL-DIALKOXYSILANE, OCTAPHENYLCYCLOTETRASILOZANE AND SYM-TETRAALKYLTETRAPHENYL-CYCLOTETRASILOXANE

[75] Inventors: Richard A. Compton, Santa Barbara; Alfred V. Belanger, Bakersfield, both of Calif.

[73] Assignee: Nusil Technology, Santa Barbara, Calif.

[21] Appl. No.: 09/458,108

[22] Filed: Dec. 8, 1999

[51] Int. Cl.$^7$ .................................. C07F 7/08; C07F 7/18
[52] U.S. Cl. ............................................................. 556/480
[58] Field of Search ............................................. 556/480

[56] References Cited

U.S. PATENT DOCUMENTS

| | | | |
|---|---|---|---|
| 4,748,262 | 5/1988 | Ishihara et al. | 556/480 |
| 4,777,278 | 10/1988 | Band et al. | 556/480 |
| 5,739,370 | 4/1998 | Razzano | 556/461 |

*Primary Examiner*—Paul F. Shaver
*Attorney, Agent, or Firm*—Klein & Szekeres, LLP

[57] ABSTRACT

Diphenyl-dialkoxysilanes and phenylmethyl-dialkoxysilanes where the alkoxy group has 1 to 10 carbons, preferably 1 or 2 carbons, are prepared by the reactions shown in Schemes 1 through 4.

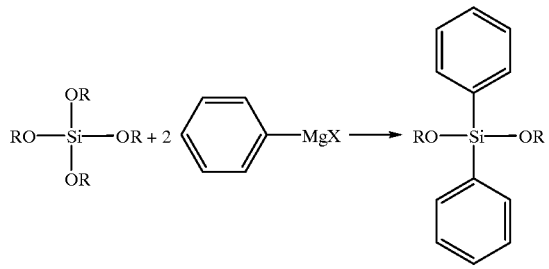

Scheme 1

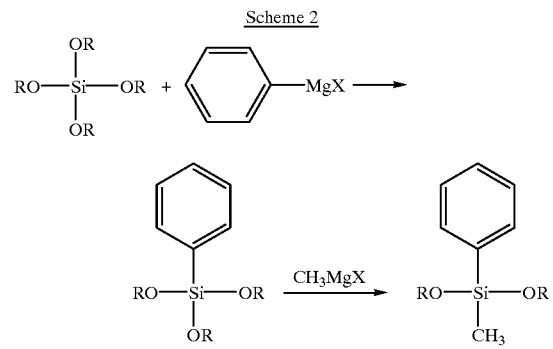

Scheme 2

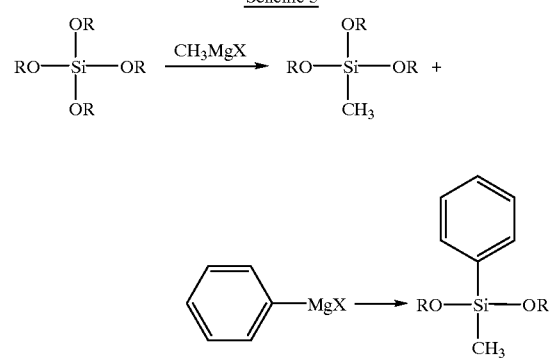

Scheme 3

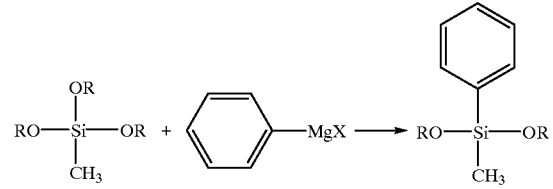

Scheme 4

20 Claims, No Drawings

PROCESS FOR PRODUCTION OF DIPHENYL-DIALKOXYSILANE, PHENYLALKYL-DIALKOXYSILANE, OCTAPHENYLCYCLOTETRASILOZANE AND SYM-TETRAALKYLTETRAPHENYL-CYCLOTETRASILOXANE

BACKGROUND OF THE INVENTION

1. Field of the Invention

The present invention is in the field of silicone and siloxane chemistry. More particularly, the present invention relates to a process for preparing diphenyl-dialkoxysilane and phenylalkyl-dialkoxysilane compounds which have their primary use in the preparation of octaphenylcyclotetrasiloxane and sym-tetraalkyltetraphenyl-cyclotetrasiloxane compounds.

2. Brief Description of the Prior Art

Octaphenylcyclotetrasiloxane and sym-tetraalkyltetraphenyl-cyclotetrasiloxane compounds are important raw or starting materials for the preparation of various siloxane containing products. U.S. Pat. No. 5,739,370 discloses a process for preparing these compounds, in which diphenyldimethoxysilane and methylphenyldimethoxysilane are converted into octaphenylcyclotetrasiloxane and sym-tetraalkyltetraphenyl-cyclotetrasiloxane, respectively. In accordance with this prior art patent, the intermediates diphenyldimethoxysilane and methylphenyldimethoxysilane are obtained by alcoholysis from the corresponding halogenated silanes, that is from dihalodiphenylsilane, and from dihalomethylphenylsilane, respectively. However, the handling of halogenated silane compounds, such as of the dihalodiphenylsilanes, and dihalomethylphenylsilanes in the process of this prior art patent, has several disadvantages, because the halogenated silanes react with atmospheric moisture to produce toxic and corrosive acids (such as hydrogen chloride) and are, generally speaking, difficult to handle. Therefore, there is a need in the art for a process of synthesizing octaphenylcyclotetrasiloxane and sym-tetraalkyltetraphenyl-cyclotetrasiloxane compounds without using halogenated silanes as the starting materials. More specifically stated, there is a need in the art for synthesizing diphenyldialkoxysilanes and methylphenyl-dialkoxysilanes as intermediates for the synthesis of octaphenylcyclotetrasiloxane and sym-tetraalkyltetraphenyl-cyclotetrasiloxane compounds while avoiding the use of halogenated silanes in the process.

SUMMARY OF THE INVENTION

The present invention relates to a process for preparing diphenyldialkoxysilanes by the reaction indicated in Scheme 1, and to the processes for preparing methylphenyldialkoxysilanes as indicated in Scheme 2, Scheme 3 and Scheme 4.

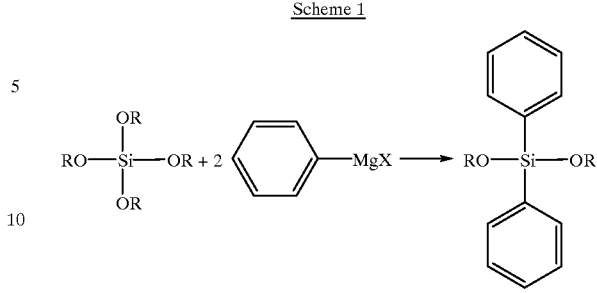

Scheme 1

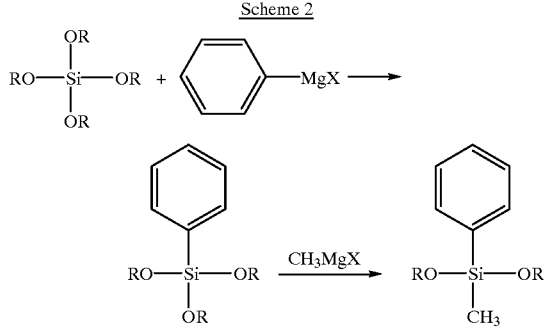

Scheme 2

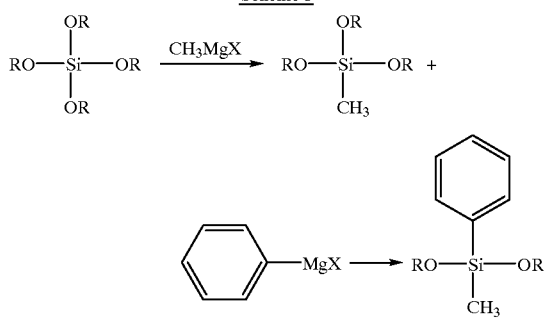

Scheme 3

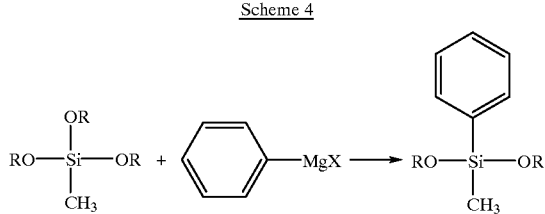

Scheme 4

The diphenyldialkoxysilanes and the methylphenyldialkoxysilanes which have been obtained in the novel process, are reacted to provide octaphenylcyclotetrasiloxane and sym-tetraalkyltetraphenyl-cyclotetrasiloxane compounds substantially in accordance with the disclosure of U.S. Pat. No. 5,739,370, as shown in Schemes 5 and 6, respectively. The specification of U.S. Pat. No. 5,739,370 is incorporated herein by reference.

In the schemes X is a halogen atom, selected from Cl, Br or I, and R is an alkyl group having 1 to 10 carbons.

DESCRIPTION OF THE PREFERRED EMBODIMENTS

The following specification taken in conjunction with the drawings sets forth the preferred embodiments of the present invention. The embodiments of the invention disclosed herein are the best modes contemplated by the inventors for carrying out their invention in a commercial environment, although it should be understood that various modifications can be accomplished within the parameters of the present invention.

Referring now to Scheme 1 set forth above, a tetraalkoxysilane is reacted with a phenyl-Grignard reagent to provide the corresponding diphenyldialkoxysilane. Tetraalkoxysilanes where the alkoxy group (R in Scheme 1) has 1 to 10 carbons are suitable for the reaction. Preferably the tetraalkoxysilane used in the reaction has alkoxy groups of 1 to 6 carbon atoms and even more preferably 1 or 2 carbons. Presently ethylorthosilicate which is commercially available is the most preferred material used in this reaction. The phenyl Grignard reagent used in the reaction may have either chlorine, bromine or iodine as the halogen, more preferably bromine or chlorine, with phenyl magnesium chloride being the presently preferred reagent. The reaction with the Grignard reagent is conducted in an aprotic ether type solvent, of which tetrahydrofuran (THF) is the most preferred. Because the reaction with the Grignard reagent tends to be exothermic, cooling may be required but the reaction can be conducted at temperatures at which the solvent refluxes, or at lower temperature, or at higher temperature (under pressure).

As is shown in Scheme 1, the reaction stochiometrically requires two moles of the Grignard reagent for each mole of tetraalkoxysilane used. However, in practice a broad range of molar equivalent Grignard reagent can be used while still obtaining the desired product. Specifically, a practical quantity of diphenyldialkoxysilane product is obtained in the reaction when approximately 1 to 3 mols of Grignard reagent is used for each mol of tetraalkoxysilane, with 1 to 2 mols being preferred, and approximately 1.5 mol being used in the example described in detail below. Those skilled in the art will readily understand that this is possible, because irrespective of the precise amount of Grignard reagent added multiple Grignard reaction products, such as monophenylated, diphenylated and triphenylated products are also formed in the reaction although in quantities which are influenced by the molar ratio of Grignard reagent added and by other reaction conditions as well. However, these products have differing volatilities (boiling points) so that the desired diphenyldialkoxysilanes can be obtained by fractional distillation. Reaction Scheme 1 indicates two mols of phenyl-Grignard in the reaction, because this is the stoichiometric amount.

The product, diphenyldialkoxysilane is typically isolated from the reaction mixture through removal of the ether type solvent by distillation, usually followed by addition of hydrocarbon-type solvent that boils higher than the ether-type solvent and distillation of more ether-type solvent from the reaction mixture. A preferred solvent used for this purpose is xylene. Distillng the ether-type solvent from the mixture containing the higher boiling hydrocarbon involves some co-distillation of the hydrocarbon as well. After the ether-type solvent is removed, magnesium salts and other possible insoluble side products are removed from the reaction mixture by filtration, and the filtrate is subjected to fractional distillation and vacuum distillation. Highly pure product is typically obtained by subjecting the fraction containing somewhat crude product to a second distillation step in vacuum. The boiling point of diphenyldiethoxysilane is approximately 156 ° C. at 25 Hgmm vacuum, the boiling point of diphenyldimethoxysilane is 150 ° C. at 25 Hgmm vacuum.

Referring now to Schemes 2 and 3 set forth above, processes for preparing phenylmethyldialkoxysilanes are disclosed. These processes uses the same tetraalkoxy silane compound(s) as starting material(s) and substantially the same reaction conditions, with such variations which will be readily apparent to the practicing chemist, as the process described above in connection with Scheme 1. However, as is shown in Scheme 2, the tetraalkoxysilane is reacted with only one equivalent of phenyl magnesium halide to first yield a phenyltrialkoxysilane, which is then reacted, preferably in situ, that is without isolating the phenylated intermediate, with one equivalent methyl magnesium halide to yield a phenylmethyldialkoxysilane compound. Alternatively, the intermediate phenyltrialkoxysilane can be isolated and thereafter reacted with methyl magnesium halide. The final product is isolated from the filtrate, after removal of ether type solvent and filtration of salts, by fractional vacuum distillation. The use of the Grignard reagents containing chlorine is preferred in this set of reactions as well. Scheme 3 illustrates the process wherein the sequence of adding the two different Grignard reagents is reversed. It is also possible within the scope of the invention to simultaneously react the tetraalkoxysilane with the two different Grignard reagents. Those skilled in the art will readily understand that in this sequence of reactions also, stochiometrically speaking one mol of each Grignard reagent is required for each mol of tetraalkoxysilane, however in practice a lesser or greater amount of each Grignard reagent may be added to the reaction mixture. The desired phenylmethyldialkoxysilane typically has different volatility (boiling point) than the side products formed in the reaction. Phenylmethyldiethoxysilane boils at 117 ° C. at 30 Hgmm vacum.

Reaction Scheme 4 illustrates still another process within the scope of the invention to synthesize phenylmethyldialkoxysilane. In this process, the starting material is alkyltrialkoxysilane, which is reacted with phenyl magnesium halide. Methyltrimethoxysilane is commercially available and is the preferred starting material in this scheme. The reaction and the isolation of the product is conducted under conditions similar to those described above.

SCHEME 5

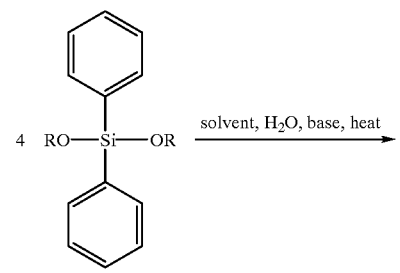

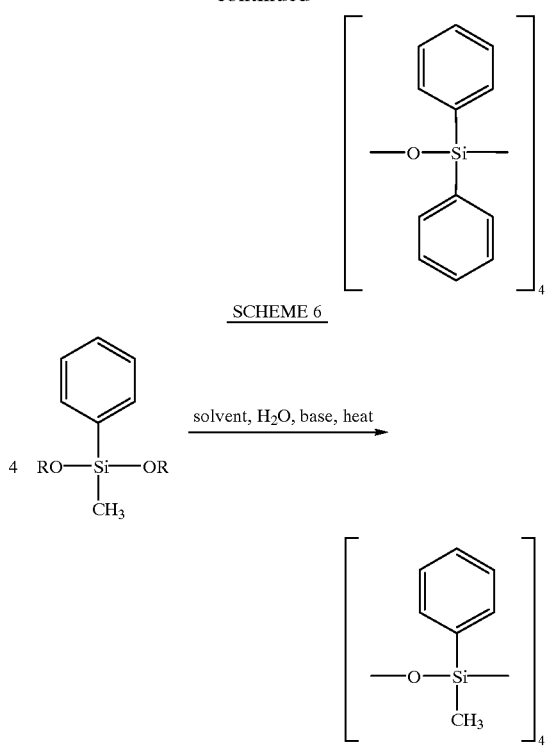

SCHEME 6

Reaction Schemes 5 and 6 illustrate the process of using the diphenyldialkoxysilanes and the phenylmethyldialkoxysilanes to make octaphenylcyclotetrasiloxane and sym-tetraalkyltetraphenyl-cyclotetrasiloxane, respectively. In these processes the diphenyldialkoxysilanes and the phenylmethyldialkoxysilanes obtained in accordance with this invention are heated with water, base and in a solvent in which the desired tetrasiloxanes are only sparingly soluble, or insoluble, as disclosed in U.S. Pat. No. 5,739,370. The resulting tetrasiloxanes serve as important raw materials in several manufacturing processes.

DETAILED DESCRIPTION OF THE PREPARATION OF DIPHENYIDIETHOXYSILANE IN ACCORDANCE WITH THE INVENTION 1.92 kilograms of 1.9 molar pheny 1 magnesium chloride solution in tetrahydrofuran was added to 25 kilograms of ethylorthosilicate in a vessel fitted with a jacket suitable for cooling and heating, and a column with condenser suitable for distillation of volatile solvents. After the addition of the phenyl magnesium chloride solution, the vessel was then heated to bring the reaction mixture to boiling and approximately 30 kilograms of tetrahydrofuran was distilled off at atmospheric pressure. Approximately 35 kilograms of xylene was added to the vessel and upon additional heating essentially all of the remainder of the tetrahydrofuran was removed from the reaction mixture by distillation. The temperature during this step was in the range of approximately 68 to 138° C. After cooling the contents were filtered to remove precipitated solids and the liquid was subjected to fractional distillation in vacuo to provide one or more fractions containing diphenyldiethoxysilane. The fraction(s) containing diphenyldiethoxysilane were purified by a second step of distillation in vacuo to give approximately 15 kilograms of diphenyldiethoxysilane (boiling point approximately 156° C. at 25 Hgmm vacum) with a purity of greater than 99.9% by gas chromatography.

The diphenyldiethoxysilane was processed further to octaphenylcyclotetrasiloxane by base catalyzed hydrolysis in water and acetone, as described in U.S. Pat. No. 5,739,370.

What is claimed is:

1. A process for the production of diphenyl-dialkoxysilane of the formula $(Ph)_2Si(OR)_2$ where Ph is phenyl and R is an alkyl group of 1 to 10 carbons, the process comprising the step of:

reacting in a reaction mixture a tetraalkoxysilane of the formula $Si(OR)_4$ with a Grignard reagent of the formula PhMgX where X is selected from the group consisting of Cl, Br and I.

2. The process of claim 1 where R is methyl or ethyl.
3. The process of claim 1 where X is chlorine or bromine.
4. The process of claim 2 where X is chlorine or bromine.
5. The process of claim 1 where the step of reacting includes heating the tetraalkoxysilane with the Grignard reagent in an aprotic ether-type solvent.
6. The process of claim 5 where the ether-type solvent is tetrahydrofuran.
7. The process of claim 5 further comprising a step of isolating the diphenyl-dialkoxysilane, said step of isolating including steps of adding to the reaction mixture a hydrocarbon solvent that boils higher than the ether type solvent, and removing the ether type solvent by distillation from the reaction mixture containing said hydrocarbon solvent.
8. The process of claim 7 where the step of isolating includes a step of removing by filtration insoluble substances that form in the reaction, said step of filtration being conducted after removal of the ether-type solvent.
9. The process of claim 8 where the ether type solvent is tetrahydrofuran and the hydrocarbon solvent is xylene.
10. A process for the production of diphenyldialkoxysilane, where the alkoxy group has 1 or 2 carbons, comprising the steps of:

reacting in an aprotic ether-type solvent an orthosilicate of the formula $Si(OR)_4$ where R is ethyl or methyl, with a phenylmagnesium halide selected from the group consisting of phenyl magnesium chloride, phenyl magnesium bromide, and phenyl magnesium iodide, said substances forming a reaction mixture;

removing the aprotic ether-type solvent from the reaction mixture, said step of removing including the steps of adding a hydrocarbon solvent that boils higher than the ether type solvent to the reaction mixture, and distilling the ether-type solvent from the mixture containing said hydrocarbon solvent;

after the step of removing the ether-type solvent removing solid substances from the reaction mixture to obtain a liquid filtrate, and isolating the diphenyldialkoxysilane from the filtrate by fractional distillation in vacum.

11. The process of claim 10 where R is ethyl.
12. The process of claim 11 where the phenyl magnesium halide is phenyl magnesium chloride.
13. The process of claim 12 where the ether type solvent is tetrahydrofuran.
14. The process of claim 13 where the hydrocarbon solvent is xylene.
15. A process for production of phenylmethyl-dialkoxysilane of the formula $PhCH_3Si(OR)_2$ where Ph is phenyl and R is an alkyl group of 1 to 10 carbons, the process comprising the steps of:

reacting a tetraalkoxysilane of the formula $Si(OR)_4$ with a first Grignard reagent that is selected from the group consisting of a phenyl magnesium halide and a methyl magnesium halide, where the halogen is selected independently from chlorine, bromine and iodine, to provide a trialkoxysilane compound having an R' substituent attached to the silicone atom, the R' substituent being one of phenyl and methyl;

reacting said trialkoxysilane compound with a second Grignard reagent selected from said group of phenyl magnesium halide and methyl magnesium halide, the second Grignard reagent being different than the first Grignard reagent, to form said phenylmethyl-dialkoxysilane.

16. The process of claim 15 further comprising the step of isolating said phenylmethyl-dialkoxysilane.

17. The process of claim 15 wherein R is ethyl or methyl.

18. A process for production of phenylmethyl-dialkoxysilane of the formula $PhCH_3Si(OR)_2$ where Ph is phenyl and R is an alkyl group of 1 to 10 carbons, the process comprising the step of:

reacting a methyltrialkoxysilane of the formula $CH_3Si(OR)_3$ with a phenylmagnesium halide selected from the group consisting of phenyl magnesium chloride.

19. The process of claim 18 where R is methyl or ethyl.

20. The process of claim 18 further comprising the step of isolating said phenylmethyl-dialkoxysilane.

* * * * *

UNITED STATES PATENT AND TRADEMARK OFFICE
CERTIFICATE OF CORRECTION

PATENT NO. : 6,160,151
DATED : December 12, 2000
INVENTOR(S) : Richard A. Compton, et al.

It is certified that error appears in the above-identified patent and that said Letters Patent is hereby corrected as shown below:

In the title [54]: "OCTAPHENYLCYCLOTETRASILOZANE" should be
—OCTAPHENYLCYCLOTETRASILOXANE—

Column 1, line 4, "OCTAPHENYLCYCLOTETRASILOZANE" should be
—OCTAPHENYLCYCLOTETRASILOXANE—

Signed and Sealed this

Eighth Day of May, 2001

Attest:

NICHOLAS P. GODICI

Attesting Officer

Acting Director of the United States Patent and Trademark Office